US00PP21497P2

(12) United States Plant Patent
Strasko et al.

(10) Patent No.: US PP21,497 P2
(45) Date of Patent: Nov. 16, 2010

(54) ***PENNISETUM* PLANT NAMED 'SKY ROCKET'**

(50) Latin Name: *Pennisetum setaceum*
Varietal Denomination: Sky Rocket

(75) Inventors: Ronald Strasko, Leola, PA (US); Karen R. Stever, Gainsville, GA (US)

(73) Assignee: It Saul Plants, Alpharetta, GA (US)

( * ) Notice: Subject to any disclaimer, the term of this patent is extended or adjusted under 35 U.S.C. 154(b) by 0 days.

(21) Appl. No.: 12/586,798

(22) Filed: Sep. 28, 2009

Related U.S. Application Data

(60) Provisional application No. 61/269,484, filed on Jun. 25, 2009.

(51) Int. Cl.
*A01H 5/00* (2006.01)

(52) U.S. Cl. ..... Plt./384

(58) Field of Classification Search ..... Plt./384
See application file for complete search history.

*Primary Examiner*—Susan B McCormick Ewoldt
(74) *Attorney, Agent, or Firm*—Penny J. Aguirre

(57) ABSTRACT

A new cultivar of *Pennisetum setaceum* named 'Sky Rocket', characterized by its variegated foliage comprised of vertical bands of green and white that typically have green centers and white margins, its height of about 1.2 meters, its blooms that are white in color and slightly tinged with purple-pink, and its very vigorous but non-invasive growth habit.

2 Drawing Sheets

Botanical classification: *Pennisetum setaceum.*
Varietal denomination: 'Sky Rocket'.

BACKGROUND OF THE INVENTION

The present invention relates to a new and distinct cultivar of *Pennisetum setaceum* and will be referred to hereafter by its cultivar name, 'Sky Rocket'. 'Sky Rocket' represents a new cultivar of purple fountain grass; a warm-season, ornamental grass grown for container and landscape use.

The Inventors discovered and selected the new cultivar, 'Sky Rocket', as a culm sport of *Pennisetum setaceum* 'Fireworks' (U.S. Plant Pat. No. 18,504) during division of a stock plant of 'Fireworks' in a nursery in Alpharetta, Ga. in March of 2009.

Asexual reproduction of the new cultivar was first accomplished by culm division in Alpharetta, Ga. in May of 2009 by one of the Inventors. Asexual propagation by both culm division and stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Sky Rocket' from all other selections of *Pennisetum* known to the Inventors.

1. The foliage of 'Sky Rocket' exhibits a distinct longitudinal banding pattern consisting of bands of bright white and green; most typically with green centers and white margins.
2. 'Sky Rocket' reaches a height of about 1.2 m (4 ft), and a spread of about 0.9 m, similar to the parent plant.
3. 'Sky Rocket' blooms heavily from May until frost in Georgia with plumes that are white in color and slightly tinged with purple-pink on the bristles.
4. 'Sky Rocket' exhibits a very vigorous growth habit.

5. 'Sky Rocket' exhibits a noninvasive growth habit as re-seeding has not been observed.

'Sky Rocket' can be most closely compared to the parent plant, 'Fireworks', which has foliage that is variegated with longitudinal stripes of white, green and burgundy and the blooms are burgundy in color rather than white tinged with purple-pink. Typical plants of the species *Pennisetum setaceum* differ from 'Sky Rocket' in having green foliage, in being shorter in height and in readily re-seeding. 'Sky Rocket' can be compared to the cultivar 'Rubrum' (not patented), which has foliage that is non-variegated and burgundy in color when grown in full sun and green in color when grown in full shade. 'Sky Rocket' can also be compared to the cultivar 'Ivory Fountain' (U.S. Plant Pat. No. 20,682), which is similar in having white flowers tinged with purple-pink, however the foliage of 'Ivory Fountain' is non-variegated and solid green in color.

BRIEF DESCRIPTION OF THE DRAWING

The accompanying colored photographs illustrate the overall appearance and distinct characteristics of plants the new *Pennisetum* as grown outdoors in spring of 2009 in a one-gallon container in Alpharetta, Ga.

The photograph in FIG. 1 was taken in early spring and illustrates the foliage coloration of 'Sky Rocket'.

Figure 1:
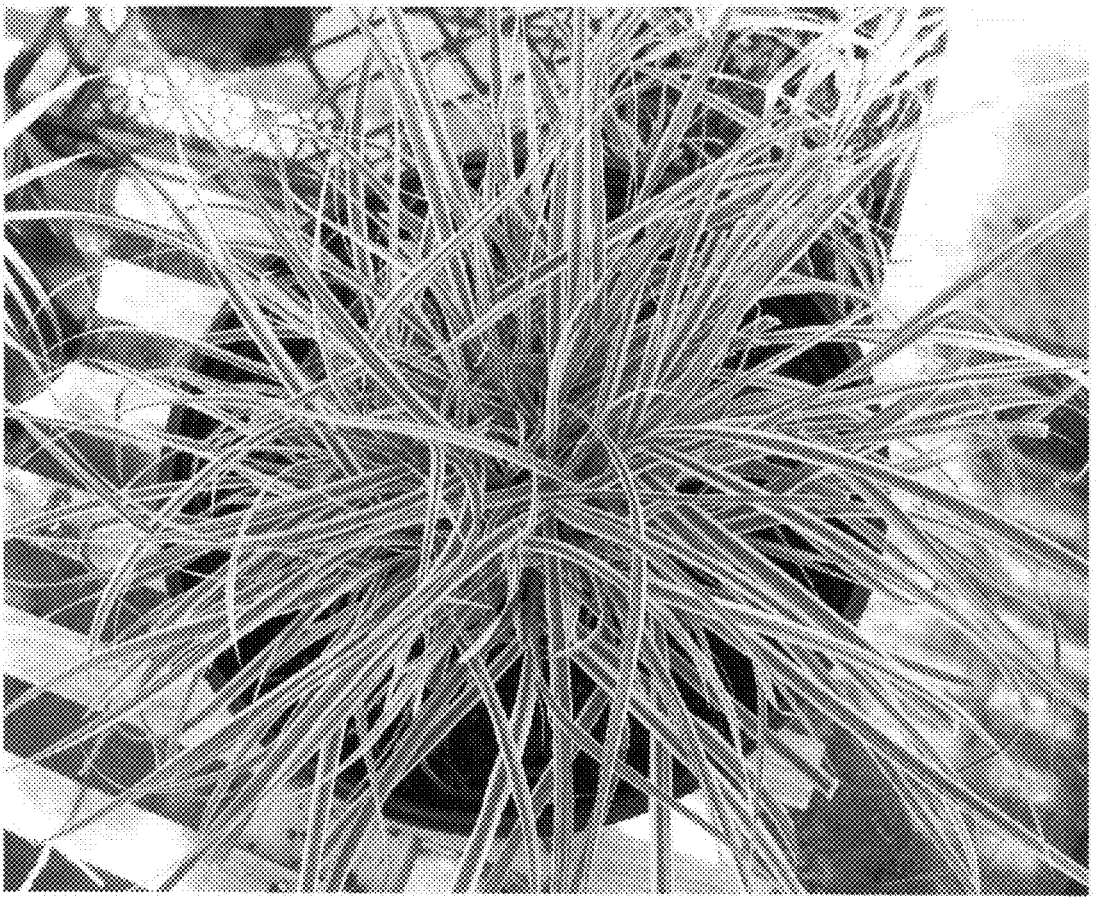
Figure 2:
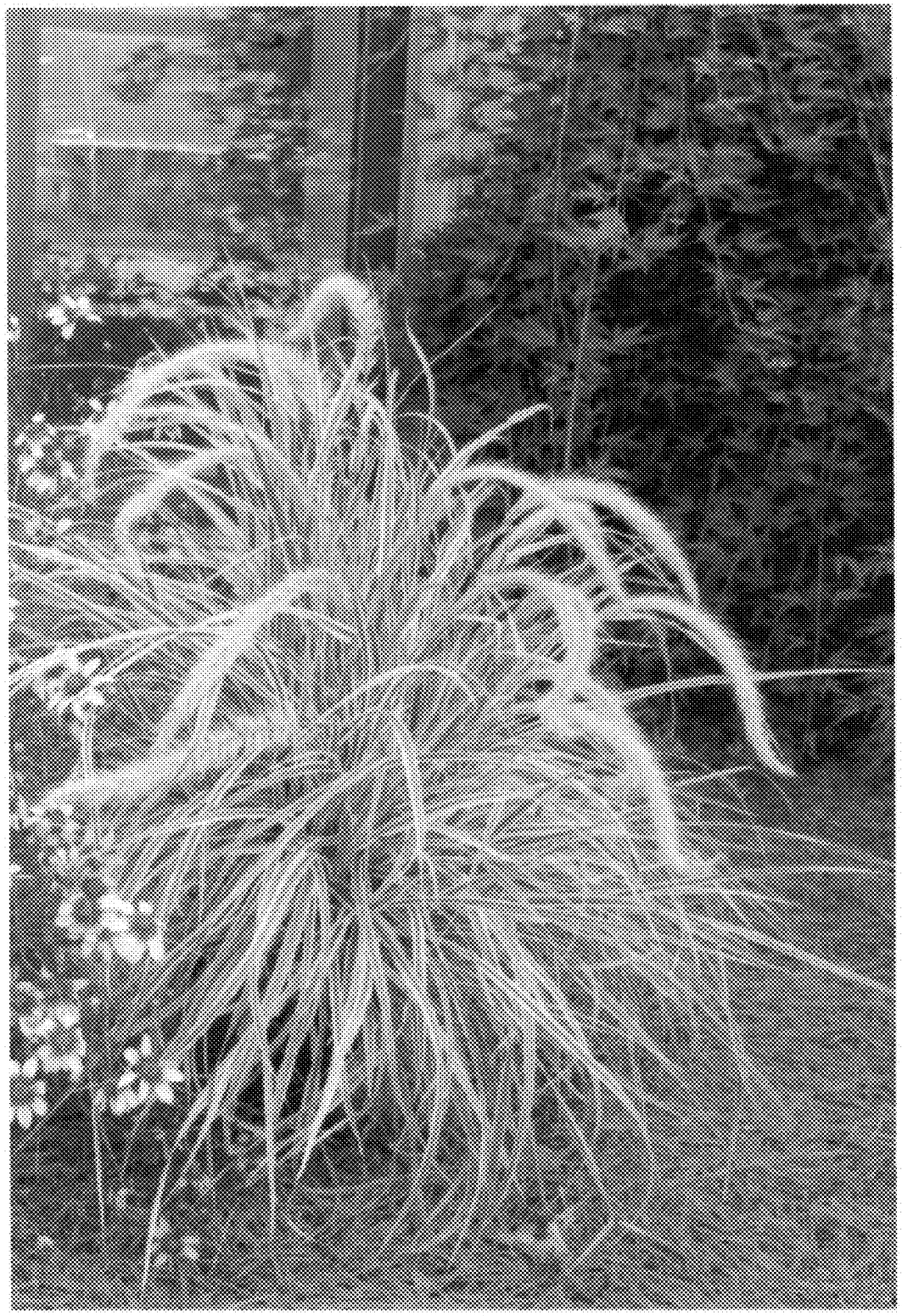

The photograph on FIG. 2 shows is a view of 'Sky Rocket' in late spring in bloom. The colors in the photographs are as close as possible with the digital photography and printing techniques utilized and the color codes in the detailed botanical description more accurately describe the new *Pennisetum.*

DETAILED BOTANICAL DESCRIPTION

The general observations and descriptions describe plants that are one year in age as grown outdoors in one-gallon containers. The new *Pennisetum* has not been observed under all possible environmental conditions and the phenotype may vary somewhat with variations in temperature, day-length, light intensity, soil types, and water and fertility levels without, however, any variance in genotype. The color determinations are in accordance with the 2007 R.H.S. Colour Chart of The Royal Horticultural Society, London, England, except where general color terms of ordinary dictionary significance are used.

General description:

*Blooming period.*—Blooms from May until frost in Alpharetta, Ga.

*Plant habit.*—Herbaceous, clump-forming, ornamental grass with an upright culms and leaf blades that cascade in a vase-shaped form.

*Height and spread.*—Reaches a height of about 1.2 m (4 ft), and a spread of about 0.9 m, plants used for data collection grown in one-gallon containers; height 58 cm in height and 45 cm in width.

*Cold hardiness.*—U.S.D.A. Zone 10, grown in colder climates as a seasonal grass.

*Culture.*—Grows best in fertile, well-drained soils in full sun, tolerant to wind but performs poorly in wet soils, foliage coloration is best in full sun.

*Diseases and pests.*—*Pennisetum setaceum* and 'Sky Rocket' have no known disease resistance or pest problems.

*Root description.*—Fibrous.

Growth and propagation:

*Propagation.*—Culm division and stem cuttings.

*Time required for root initiation.*—From a full fan division, roots appear within 7 days in a propagation house heated to 75° F., cutting initiate roots within 14 days.

*Time required for root development.*—Roots will fully develop a 72-cell liner in 4 to 5 weeks, and a rooted 72-cell liner will fully develop in a 4 inch container in 5 to 6 weeks.

*Growth rate.*—Very vigorous, plants obtain mature height and flower in one growing season.

Culm (stem) description:

*General.*—Cylindrical, enclosed by leaf sheaths.

*Culm aspect.*—Held erect to slightly cascading.

*Culm color.*—Ranges from 144B to 137C (comprised of leaf sheaths).

*Culm size.*—An average of 34 cm in length and an average of 5 mm in width.

*Culm surface.*—Glabrous and satiny.

*Internode length.*—Average of 5.5 cm.

Foliage description:

*Leaf shape.*—Linear.

*Leaf division.*—Simple.

*Leaf base.*—Sheathed.

*Leaf apex.*—Acute, tapering to a fine point.

*Leaf aspect.*—Emerging leaves are erect, leaf blades diverge from leaf sheath at ligule at about a 40° angle from center of culm then gently cascading, blades are flat to slightly concave.

*Leaf venation.*—Parallel, mid rib is recessed on upper surface, color matches the color of the leaf blades on upper and lower surface.

*Leaf margins.*—Entire in appearance but finely scabrous to touch.

*Leaf persistence.*—Foliage dries but is persistent throughout the winter.

*Leaf attachment.*—Sheathed, leaf is sheathed from the base of culm and the blade extends out from the culm at a ligule.

*Ligule.*—Average of 2 mm in width, extends the entire length of leaf blade, 144D in color.

*Leaf size.*—Average of 34 cm in length and up to 1.2 cm in width; narrower at culm attachment and tapering to a point at the apex.

*Leaf surface.*—Glabrous on upper and lower surface with satin sheen.

*Leaf number.*—Average of 5 leaves per culm 34 cm in length.

*Leaf arrangement.*—Alternate, 2 ranked.

*Leaf color and variegation pattern.*—Variegation is composed of vertical bands of green and white of varying widths; most typically with green centers and white margins, variegation pattern and coloration occurring on upper and lower surface, new leaves; green band are a blend of 144A and 138A, white bands 155A, mature leaves; green band are 137A and 137B in color and the white bands are 155A in color.

Flower description:

*General description.*—Inflorescence is a plumed raceme terminating from each culm, arching upward and then cascading, comprised of densely packed spikelets surrounded by an involucre of bristles.

*Lastingness of inflorescence.*—Racemes dry but remain persistent.

*Fragrance.*—None.

*Panicle size.*—An average of 25 cm in length and an average of 3.5 cm in width (including bristles).

*Panicle color.*—Effectively 155A and tinged with N77C due to bristles, becoming more beige color with maturity (effectively 158A in color), rachis is about 1.5 mm in width and 137C in color.

*Spikelet description.*—Single or in groups of 2 to 3, an average of 1.2 mm (2.7 cm including bristles) and 1.5 mm in width (5 mm including bristles), 2 glumes; membranous, transparent and 155A in color, one is 4 mm in length and 1 m in width and one is about 6 mm in length and 1.5 mm in width, palae; about 5 mm in length and 1.5 mm in length, lemma; translucent and about 155A in color, about 5 mm in length and 1.2 mm in width, bristles; attached to base of spikelet, up to 3.2 cm in length, unequal in length, plumose at base, 155A in color and becoming tinted with N77C.

*Reproductive organs.*—Pistil; 1 with two plumose stigmas that are 6 mm in length, 0.4 mm in width and 155A in color, stamens; 2, shorter that stigmas, 1.8 mm in length, 0.5 mm in width and 152C in color, pollen; not visible, seed; seed set was not observed.

It is claimed:

1. A new and distinct cultivar of *Pennisetum* plant named 'Sky Rocket' as herein illustrated and described.

* * * * *